United States Patent
Newhouse et al.

(10) Patent No.: US 6,470,882 B1
(45) Date of Patent: *Oct. 29, 2002

(54) PERNASAL APPLICATION OF AEROSOL MEDICATION

(76) Inventors: Michael T. Newhouse, 436 Queen Street South, Hamilton, Ontario (CA), L8P 3T9; Israel Amirav, Hanarius 41, Rosh Pina 12000 (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/939,283

(22) Filed: Sep. 29, 1997

(51) Int. Cl.[7] .................. A61M 15/00; A61M 16/00; A62B 18/00; A62B 7/00; A62B 9/00

(52) U.S. Cl. .................. 128/200.24; 128/203.12; 128/203.29

(58) Field of Search ............ 128/203.29, 203.18, 128/203.22, 206.28, 206.29, 200.24, 203.12

(56) References Cited

U.S. PATENT DOCUMENTS

| | | | | |
|---|---|---|---|---|
| 700,528 A | * | 5/1902 | Maurer | 128/204.12 |
| 815,510 A | * | 3/1906 | Coburn | 128/204.12 |
| 1,040,311 A | * | 10/1912 | Halloran | 128/204.12 |
| 1,740,083 A | * | 12/1929 | Galvin | 128/204.12 |
| 4,475,559 A | * | 10/1984 | Horn | 128/207.18 |
| 4,809,692 A | * | 3/1989 | Nowacki et al. | 128/206.24 |
| 4,832,015 A | * | 5/1989 | Nowacki et al. | 128/205.23 |
| 5,535,741 A | * | 7/1996 | Widerstrom et al. | 128/206.21 |
| 5,752,510 A | * | 5/1998 | Goldstein | 128/207.18 |
| 5,810,000 A | * | 9/1998 | Stevens | 128/200.26 |
| 5,810,003 A | * | 9/1998 | Findlater | 128/203.12 |

* cited by examiner

Primary Examiner—John G. Weiss
Assistant Examiner—Joseph F. Weiss
(74) Attorney, Agent, or Firm—Hoekendijk & Lynch, LLP

(57) ABSTRACT

The invention shows means for holding a cylindrical medicine expansion chamber and spaced from it a cylindrical body having a nipple. The medication chamber has a mask which will just fit over a baby's nose with very little clearance. The medication chamber and the bottle are received in a holder having front and back walls, and set screws to push the medication holder and bottle against the adjoining walls.

6 Claims, 3 Drawing Sheets

Figure 3:
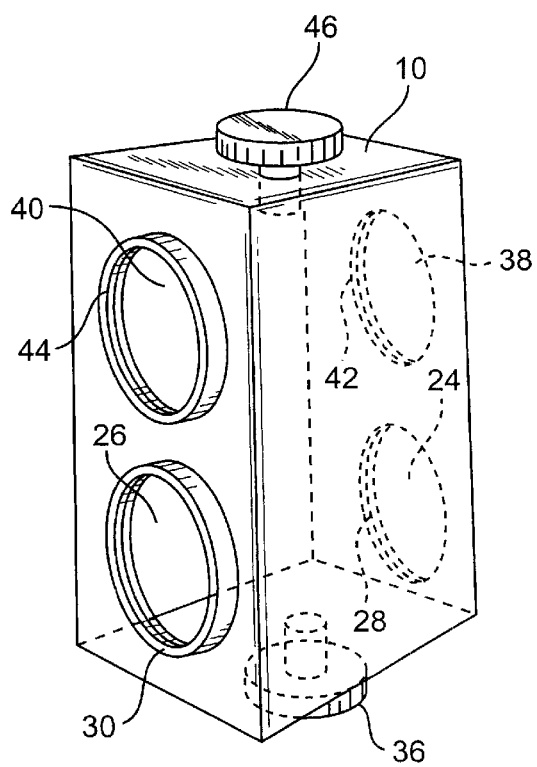
Figure 5:
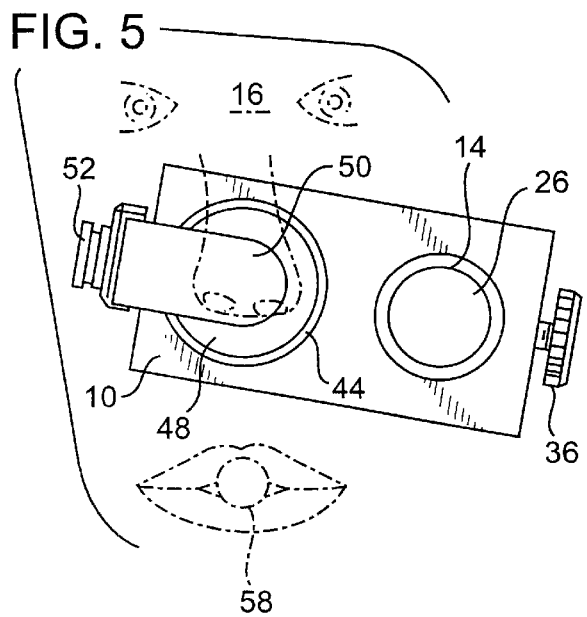
Figure 4:
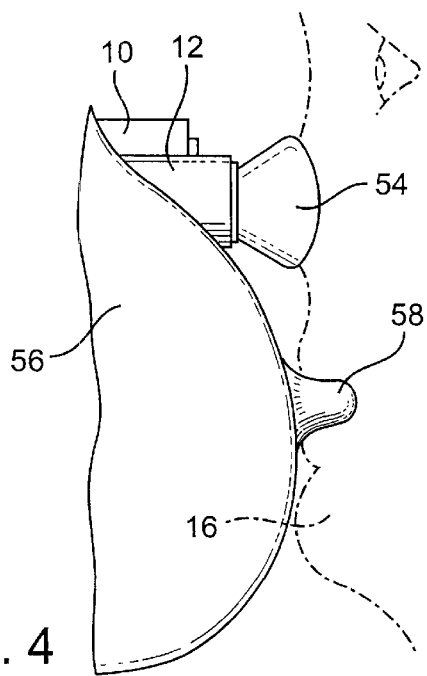

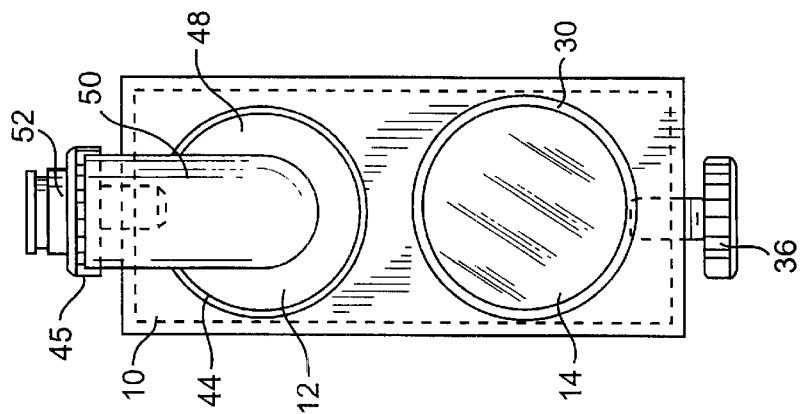
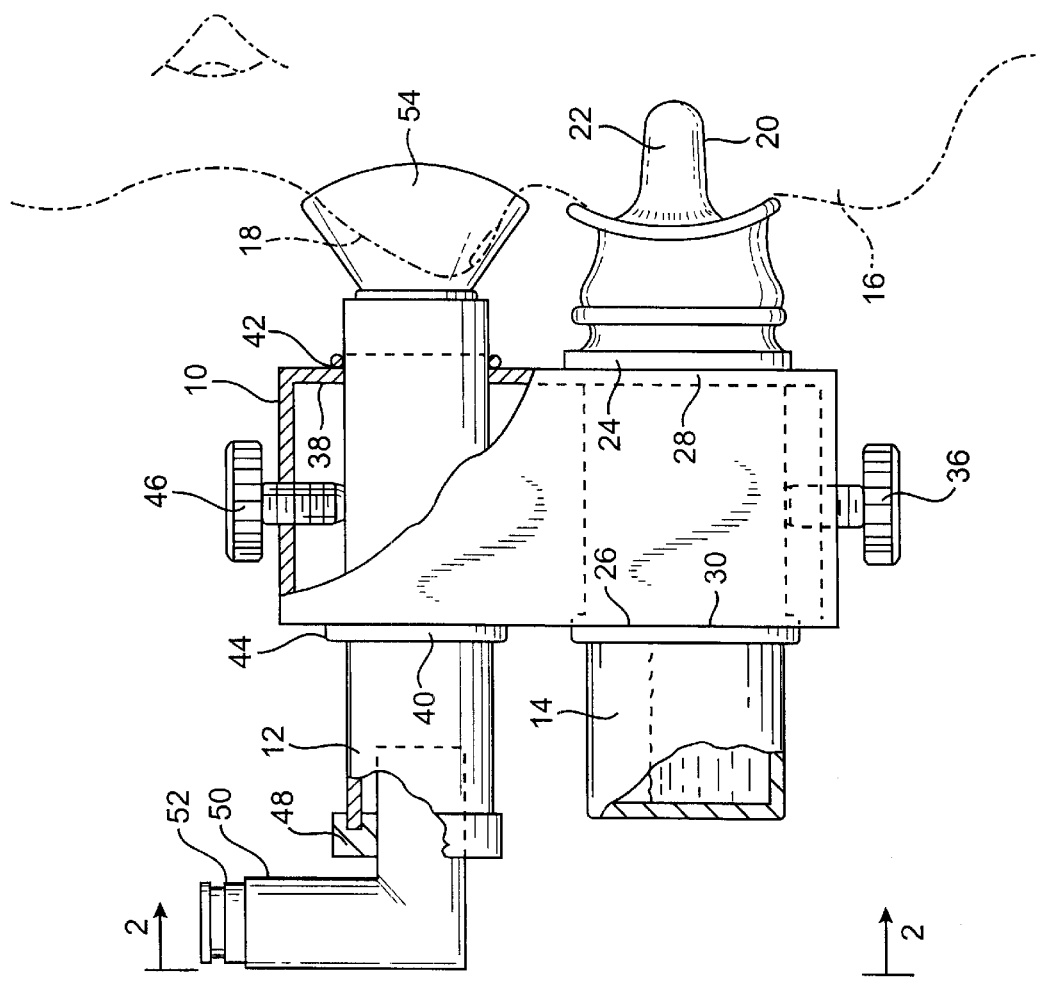
FIG. 2
FIG. 1

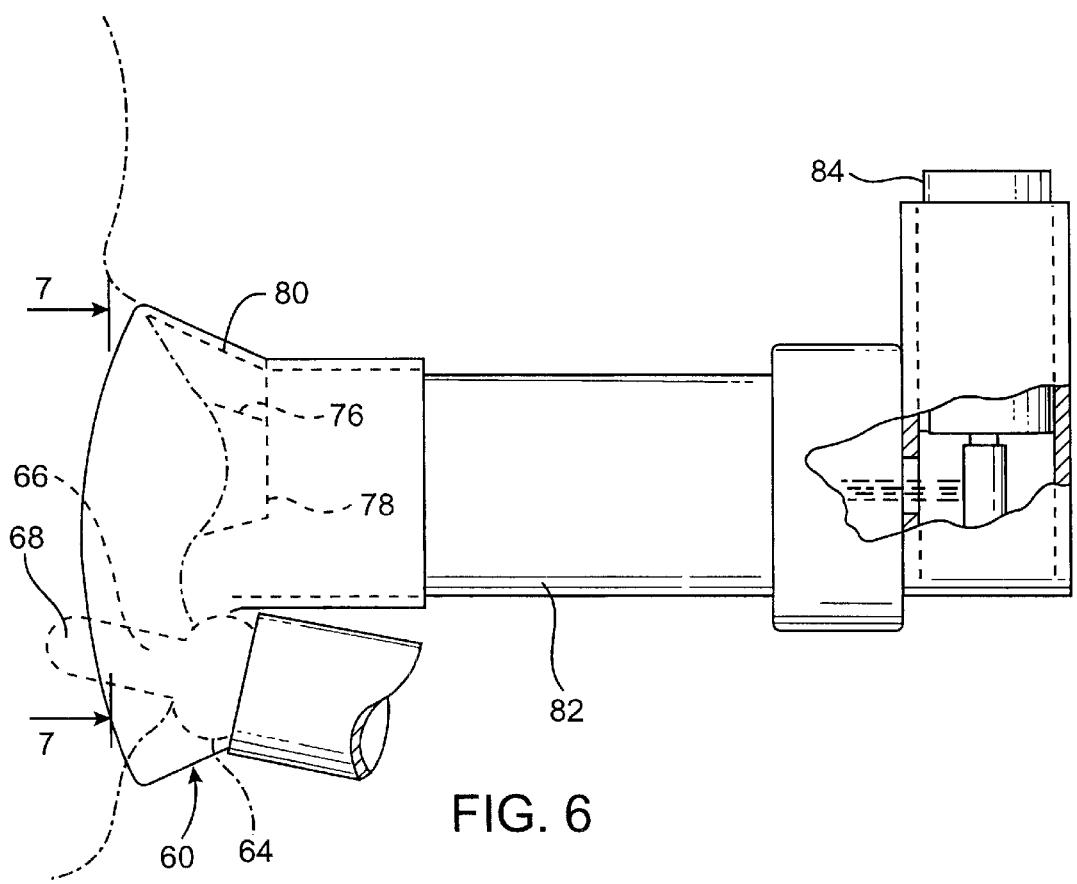
FIG. 6
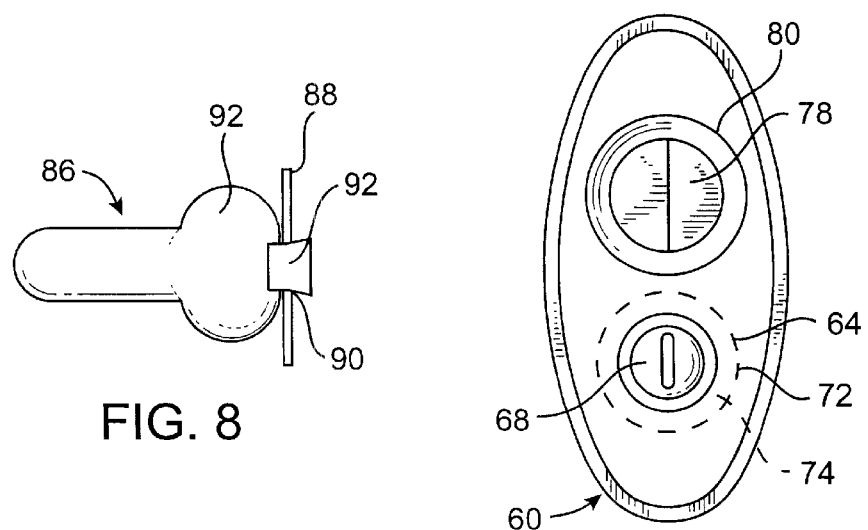
FIG. 8
FIG. 7

PERNASAL APPLICATION OF AEROSOL MEDICATION

BACKGROUND OF THE INVENTION

Aerosol medications of all kinds are used to treat lung diseases or use the lung as a portal of entry to treat systemic disease. One of the most important conditions for which aerosols are used commonly is asthma, a condition for which first line therapy is inhaled $beta_2$-agonist bronchodilators and inhaled steroids. Asthma is a very common condition in babies and infants, more common than in older children or adults. However, most devices for administering aerosol medication to babies are derived from those developed initially for delivery of asthma medication to adults and older children. Most, if not all, such devices, whether liquid nebulizers or designed for use with metered dose inhalers (MDIs) include the use of masks covering the mouth and the nose for the delivery of the medication. However, recent studies have shown by means of radiolabelled medication of aerosol delivery to the lungs, that the use of current masks is inefficient with newborns and other very young infants, most of the medication being deposited on the infant's face. Furthermore, babies tend to object to having a face mask firmly applied to their face and often begin to cry. These factors greatly decrease the efficiency of aerosol medication delivery to their lungs.

If a nebulizer and face mask are used to provide inhaled aerosols to a spontaneously breathing infant, it is vital that the mask be snugly attached to the face to insure adequate delivery. Studies have shown that with liquid nebulization even a 1 centimeter distance from the face decreases the dose delivered by 50 percent or more. Furthermore, nebulizers in infants tend to have the same disadvantages as in older children, namely, high cost, need for a power supply, lack of portability, complexities of assembly, loading and duration of administration. Infants are not very patient and do not like to sit still for prolonged periods of 10 to 20 minutes usually required for nebulization of liquid solutions. This makes the MDI with a valved holding chamber and mask the delivery system of choice in this age group.

The addition of a face mask to conventional valved holding chambers has gained considerable acceptance from practitioners for the treatment of infants. However, it is recognized that the presently available devices are less than ideal because infants do not readily accept the face mask "at least initially". For infants up to the age of about two years the mask must remain on the face tightly for at least three to six breaths, approximately 20 to 30 seconds, which may be difficult to achieve with a squirming and often crying infant at least until he gets used to it.

Infants prefer to breathe through the nose until at least 18 months of age and are easily capable of sucking from the breast or bottle while breathing normally. Sucking is a very soothing activity for most babies. Sucking is performed during feeding or as a pacifier. We have designed devices that will allow a combination of sucking activity of the baby while at the same time ensuring that medication is delivered to the respiratory tract of the infant while the infant is relatively content. The devices are comprised of a 145 milliliter widely used valved holding chamber attached to a nasal mask (aerochamber).

Alternatively the holding chamber may not have an integral valve, but both its inhalation and exhalation valves could be contained within the masks. When the baby sucks on the bottle or soother, the mask is pulled tightly onto the nose, and surrounds the nostrils of the baby, which ensures that the aerosol that has been sprayed into the holding chamber will be drawn into the baby's lungs with each breath through the nose during approximately 20 seconds (five to six breaths). A mask and holding chamber would have an attachment that would extend downwards around the baby bottle or come onto the nipple so that any feeding bottle or nipple could be used. A set screw would allow the bottle to be adjusted in such a manner that the nasal mask would fit snugly, but without undo pressure around the infant's nostrils when the nipple of the bottle or soother is being sucked on vigorously. The resulting self-administered (but caregiver facilitated) seal between the mask and the face around the nostrils would provide an excellent opportunity for actuation of the metered dose inhaler into the aerosol holding chamber, and delivery of the medication when the baby inhales during approximately five or six breaths.

Most babies and infants are obligatory nose breathers most of the time (with the exception of infants with nasal obstruction due to the common cold, etc., or while crying) and it is therefore more logical to emphasize the nasal route for inhalation when devising an MDI accessory aerosol delivery system. Indeed, even when a face mask is used, the aerosol is actually inhaled most of the time through the nose. The face mask thus has a much larger dead space than necessary, which in situations of low tidal volume such as in neonates or infants can considerably reduce the efficiency of delivery of aerosol medication. A small mask that preferentially directs the aerosol towards the infant's nose is thus superior to a face mask. Furthermore, aerosol delivered by means of a face mask must pass across the lower half of the face to get to the nostrils. Much of the steroid is thus actually delivered to the skin of the face, and there have been case reports of steroid side effects such as acne under these conditions. By using a nasal mask or a system that directs the aerosol towards the nose, this problem would be minimized or eliminated since the aerosol would pass directly into the nares and from there into the lungs.

By way of background, inhaled therapy is the main,stay of asthma management. Traditionally, most inhaled medication has been delivered by small volume wet nebulizers which are relatively bulky, expensive and not always available when needed because of limited to their portability. Metered dose inhalers are much more efficient, convenient and less expensive. The main problem with "press and inhale" metered dose inhalers is a need to coordinate aerosol discharge and inhalation. This problem has been solved in recent years by valved holding chambers that can be filled with aerosol from which the patient inhales, and thus receives medication. These devices disassociate aerosol delivery into the aerosol holding chamber from inhalation, and so improve the reliability of aerosol administration. The use of a one way valve system provides for inhalation from the aerosol holding chamber during normal breathing followed by exhalation via another valve in the mask. This permits aerosol to be delivered to infants and children during tidal breathing provided that an appropriate mask is used to seal the innerface between the aerosol delivery system and the infant's face around the mouth and nose. This system works very well with older children and adults who can be taught to inhale by mouth. However, it is less effective with neonatals and newborns who preferentially breathe through the nose.

SUMMARY OF THE PRESENT INVENTION

It is the principal object of the present invention to utilize a nasal mask with an existing aerochamber The nasal mask directs the aerosol of medication droplets or dry particles to the nose and thus does not deposit medication on parts of the face remote from the nose. It also has the smallest total mask volume and thus smallest dead space of any inhaler system used for delivering medication to infants.

Furthermore, it is an object of the present invention to provide an adapter for holding a nasal applicator, and for also holding a bottle of milk or water or infant soother (rubber or plastic nipple) to ensure that the nasal mask is applied by the sucking activity of the infant (a soothing activity for a young child).

The nasal mask which we use is attached to an aerosol holding chamber having a volume of 25 milliliters to 250 milliliters. There is an inspiratory and expiratory valve integral to the mask or to the device, or there may be an inspiratory valve on the holding chamber and an expiratory valve as an integral part of the nasal mask to insure that the aerosol is delivered to the infant on inspiration only. The nasal mask would have an important advantage of greatly reducing the volume of the mask dead space, compared to the usual face mask (from about 15 to 50 milliliters, to about 5 to 10 milliliters) and so improve aerosol delivery efficiency. This is very important for improving aerosol therapy in infant patients. An additional advantage that would be extremely important to the patient is the combination of the nasal mask for aerosol delivery with an infant bottle and rubber nipple, or soother, so that when the infant sucks the nasal mask is applied firmly to the face around the nose. Infants up to the age of about 18 months are virtually obligatory nose breathers, so the aerosol would be delivered efficiently to a relatively contented child. It has been shown that if the infant is presented with aerosolized medication while it is crying, virtually none of the drug gets to the lungs. By contrast, if the child is breathing quietly and is comfortable the aerosol delivery to the lungs is relatively efficient.

To these ends, the principle of exclusively nasal administration of aerosolized medication is combined with a technique for the child to suck while breathing the medication. All of the possible permutations and combinations such as the use of a bottle with liquid in it and a rubber nipple, or even the possibility of breast feeding while the nasal mask is applied to the nose, are to be considered. Alternatively, a soother could be clamped to the nasal mask.

Furthermore, the invention is applicable to the use of either wet medication, or dry, powdered medication.

BRIEF DESCRIPTION OF THE DRAWING FIGURES

The present invention will best be understood with reference to the following drawings when taken in connection with the ensuing specification, wherein:

FIG. 1 is a elevation side view, partially end in section, showing the use of the mask with a holding chamber and also a bottle of milk or water;

FIG. 2 is an end elevation view taken along the lines 2—2 in FIG. 1;

FIG. 3 is a view in perspective of the holding device for the mask and a bottle;

FIG. 4 is a side elevation view similar to FIG. 1 showing the nasal mask as used with breast feeding;

FIG. 5 is an end elevation view taken from the left side of FIG. 4, showing how the device would be oriented with breast feeding;

FIG. 6 is a side elevation view of an alternative embodiment of the invention;

FIG. 7 is an end elevation view of the embodiment of FIG. 6 viewed along lines 7—7 in FIG. 6; and FIG. 8 is a side elevations view of a self-contained nipple.

DETAILED DESCRIPTION OF THE PREFERRED EMBODIMENTS

Reference first should be had to FIGS. 1–3, wherein there is shown a typical embodiment of the present invention. The device shown includes a holder 10 for two vessels. The holder 10 includes devices for securing a holding chamber 12 and a bottle 14. The holding chamber 12 may be built along the lines taught by Nowacki, et al., in U.S. Pat. No. 4,470,412 and includes an inhalation valve at the exit end of the structure. The devices are all applied to a baby or infant 16 having a nose 18 and a mouth 20.

The bottle 14 may be of uniform diameter and cylindrical, and has at the exit end a nipple 22 intended to be held in the mouth of the child. Aligned holes 24 and 26 are provided in the exit and entrance walls of the holder 10 which is shown as being of rectangular construction. O-rings 28 and 30 fit in these holes to receive the bottle 14. These O-rings provide a loose fit for the bottle 14, and a set screw 36 bears against the side of the bottle to clamp it in place, taking up the loose fit of the O-rings 28 and 30.

Above the openings for the bottle there are openings 38 and 40 in the end walls of the rectangular holder 10. O-rings 42 and 44 are received in the holes 38 and 40 to provide a loose fit for the chamber 12, which is adapted to receive the medication. The O-rings 42, 44 receive the body of the chamber 12, which is cylindrical in shape, and a setscrew 46 bears against the side of the chamber 12 to hold it in the O-rings.

At the inlet of the chamber 12 there is a universal back 48 made of rubber and adapted to receive an L-shaped fitting 50, as shown in FIG. 1. The fitting 50 is configured to carry a replaceable MDI 52 (Metered Dose Inhaler). The Metered Dose Inhaler contains a certain amount of asthma medication, and when one pushes down on the MDI a metered dose of aerosolized medication is discharged into the interior of the chamber 12, The MDI may be of the type that holds a liquid droplet aerosol, or it may be designed to contain a dry powder. The chamber 12 is large enough that the medication is thoroughly dispersed with the air within the chamber before it is inhaled.

At the exit end of the chamber 12 there is a nasal mask in the form of a cup-shaped housing 54 which fits over the nose 18 of the infant, preferably leaving little room around the nose to minimize the dead space of the mask, as discussed above, This results in efficient aerosol delivery, yet there is very little exposed skin which can be contacted by the medication dispensed by the chamber 12. Most of the medication thus enters the infant's nose directly and much more of it is deposited in the infant's or baby's lungs, thereby greatly improving the efficiency of the device. Also, there is much less chance of steroid effect on the skin as so little skin is exposed to the drug particles.

Referring to FIGS. 4 and 5, the holder 10 may be used without change even while the baby is nursing at the mother's breast 98 with a nipple 58 inserted in the baby's mouth. It is only necessary to pivot the device a few degrees about the chamber 12 to retain a good fit of the mask 54 on the baby's nose, with the bottle 14 pivoted somewhat away from the mother's breast. The bottle 14 may either remain in place in its holder, as shown, or it may be removed from the holder 10 prior to use of the device with breast-feeding. Whether the baby is receiving milk from the mother's breast, or milk or water from a bottle, or even sucking on a rubber or plastic nipple, such as from a pacifier, she will be soothed. She will not be frightened or in an anxious state from the mask 54 (which receives medication from the chamber 12 placed over her nose. As such, in contrast to current devices, the invention will allow the baby to almost certainly tolerate the 20 seconds of drug administration (5–6 breaths) and, therefore, is more likely to improve asthma control or provide relief from an asthma attack.

It will be understood that the mask 54 may be supplied in different sizes and possibly shapes to accommodate the nose of any baby imaginable, and said nipples may also occur in different sizes for different size children.

Another embodiment of the invention makes use of a nipple actually built into the mask. In an alternative construction of the invention, the mask is still applied to the face (as with current nose/mouth masks) but an inner mask configured to fit around the nose is located within the outer mask, The soother can be molded into the rim of the mask, becoming a permanent part of it. Alternatively, an opening in the mask rim would allow the nipple of the baby bottle to be inserted to provide milk (or water) while sucking. This would pull the mask towards the infant's face and form a seal against the skin (aided if necessary by the mother or other caregiver).

With reference to FIGS. 6 and 7, one possible construction according to such alternative embodiments includes an aerochamber 82 in communication with a source of medication 84 and a face mask 60. An outer molded part of the face mask 60 is provided with an integral socket 80 designed to hold the aerochamber 82, the latter having an L-shaped fitting to receive an MDI (metered dose inhaler) 84. The face mask 60 supports a nasal mask 78 which is adapted to be placed over a baby's nose without surrounding the baby's mouth, The face mask 60 is molded rubber or plastic and is shaped as an oval funnel (i.e., it is higher than it is wide) designed to fit over both the nose and mouth of a baby or infant.

The nasal mask 78 will flex up and down to a limited degree to ensure that it is a proper fit on the nose due to the rubber or plastic nature of the material of the molding 68, while the rim of the molding seals out the ambient air. The nasal mask 78 operates the same as the nasal masks 12, 54 described above.

At a lower part of the face mask 60 is a portion 64 configured and shaped to hold a nipple 66 with the tip 68 of the nipple in the baby's mouths The nipple 66 will act as a pacifier and has a flange 74 (FIG. 7) coupled to the mask portion 64. The nipple 66 also has a bulbous part 72 disposed opposite the tip 68 and received in the mask. In an alternative arrangement (not shown), the nipple 66 may be attached to a baby bottle by the bulbous part 72 of the nipple (FIG. 7) and the flange 72. A double (or split) wall 74 extends against the bottom of the nipple to insure resistance to sucking on the nipple.

In use, the small mask 78 is designed to just fit over the baby's or infant's nose and will be pulled in to form a very close fit with the nose upon inhalation. The outer molded part of the face mask is provided with an integral socket 80 designed to hold an aerochamber 82, having an L-shaped fining to receive an MDI (metered dose inhaler) 84. The nasal mask 78 will flex up and down to a limited degree to ensure that it is a proper fit on the nose due to the rubber or plastic nature of the material of the molding, while the rim of the molding seals out the ambient air, The face mask 78 operates the same as the face mask 54 to deliver medication to the baby's nose during inhalation.

FIG. 8 illustrates a design for a self-contained nipple 86 which can serve either of two purposes in the invention. The nipple 86 can be used independently of the mask, or it can be positioned anywhere on the mask and used without a bottle attached to it.

For example, in the embodiment of FIG. 6, the nipple and the bottle may be considered to be a bit crowded. The mask may be partly cut away to leave room for positioning the nipple, or the mask may be omitted by mothers who have skilled hands. The nipple 86 in FIG. 8, which is not attached to a bottle and is completely self-contained, has its base closed off by a flange or wall 88 having a hole 90 into which a cork 92 (either real or synthetic) is inserted to close off the milk-holding portion 92 of the nipple. A few ccs of milk can be stored in the portion 92 of the nipple, which is a sufficient amount to allow a baby to nurse while taking medication. Either mask 54 or 80 is applied to the infant's face or nose independently of the nipple 86 to allow such nursing, or the nipple 86 can be coupled to any area of the mask, as described above.

It will be noted that, as used in the claims, the term aerosolized medication encompasses both wet and dry medications. The particular forms and embodiments of the invention shown herein are for illustrative purposes only. Various changes will occur to those skilled in the art and will be understood as forming a part of the present invention insofar as they fall within the spirit and scope of the appended claims.

The invention is claimed as follows:

1. A method for delivering medication to a human infant or baby while allowing the infant or baby to use a soother device, the method comprising steps of:

(a) providing a nasal mask sized and configured to be placed over an infant's nose without surrounding the infant's mouth, the nasal mask being adapted to be placed in communication with a source of medication;

(b) providing a soother device adapted to be sucked on by an infant;

(c) placing the nasal mask over the infant's nose;

(d) placing the soother device in the infant's mouth; and (e) delivering medication to the nasal mask to allow the infant to breathe in the medication through its nose while sucking on the soother device.

2. The method of claim 1, wherein as a result of step (d) the infant sucks on the soother device and pulls the nasal mask against the infant's face to form a substantially sealed space to receive the medication.

3. The method of claim 2, wherein steps (c) and (d) are performed simultaneously.

4. The method of claim 1, wherein step (a) is performed by providing a nasal mask comprising a chamber adapted to receive medication, and step (e) is performed by coupling the chamber to a metered dose inhaler.

5. The method of claim 4, wherein step (e) is performed by delivering asthma medication to the chamber of the nasal mask.

6. The method of claim 1, wherein the nasal mask is placed according to step (c) to form a sealed space having a volume in the range of from about 5 to about 10 milliliters.

* * * * *